United States Patent [19]
Livant

[11] Patent Number: 5,840,514
[45] Date of Patent: Nov. 24, 1998

[54] METHODS OF TESTING CANCER CELLS AND ANTICANCER DRUGS

[75] Inventor: Donna L. Livant, Ann Arbor, Mich.

[73] Assignee: The Regents of the University of Michigan, Ann Arbor, Mich.

[21] Appl. No.: 754,322

[22] Filed: Nov. 21, 1996

[51] Int. Cl.$^6$ .................... C12Q 1/02; C12Q 1/00
[52] U.S. Cl. .................... 435/29; 435/4; 530/300; 530/323; 530/324; 530/325; 530/326; 530/327; 530/328; 530/329; 530/330; 530/350; 530/382; 514/2; 514/21
[58] Field of Search .................... 435/29, 4; 530/300, 530/323, 324, 325, 326, 327, 328, 329, 330, 350, 382; 514/2, 21

[56] References Cited

U.S. PATENT DOCUMENTS

| | | | |
|---|---|---|---|
| 4,016,043 | 4/1977 | Schuurs et al. | 195/103.5 R |
| 4,018,653 | 4/1977 | Mennen et al. | 195/127 |
| 4,424,279 | 1/1984 | Bohn et al. | 436/534 |
| 5,051,448 | 9/1991 | Shashoua | 514/547 |
| 5,169,862 | 12/1992 | Burke, Jr. et al. | 514/450 |
| 5,192,746 | 3/1993 | Lobl et al. | 514/11 |
| 5,264,358 | 11/1993 | Doersen et al. | 435/240.2 |
| 5,436,221 | 7/1995 | Kitaguchi et al. | 514/12 |
| 5,492,890 | 2/1996 | Ginsburg et al. | 514/12 |
| 5,523,209 | 6/1996 | Ginsberg et al. | 435/7.2 |
| 5,539,085 | 7/1996 | Bischoff et al. | 530/350 |
| 5,548,062 | 8/1996 | Isoai et al. | 530/326 |
| 5,559,103 | 9/1996 | Gaeta et al. | 514/54 |
| 5,576,423 | 11/1996 | Aversa et al. | 530/388.75 |

OTHER PUBLICATIONS

P. Calabresi and B.A. Chabner, "Antineoplastic Agents," In: *Goodman and Gilman The Pharmacological Basis of Therapeutics* (Pergamon Press, 8th Edition) (pp. 1209–1216) (1985).

J.H. Gerlach et al., "Multidrug Resistance," *Cancer Surveys*, 5:25–46 (1986).

J.H. Goldie and Andrew J. Coldman, "The Genetic Origin of Drug Resistance in Neoplasms: Implications for Sstemic Therapy," *Cancer Research*, 44:3643–3653 (1984).

(List continued on next page.)

*Primary Examiner*—Louise N. Leary
*Attorney, Agent, or Firm*—Medlen & Carroll, LLP

[57] ABSTRACT

The testing of tumor cells, including human tumors capable of metastases, in assays employing fibronectin-depleted substrates is described. Ex vivo induction of cells, including biopsied human cells, is performed with invasion-inducing agents.

11 Claims, 4 Drawing Sheets

OTHER PUBLICATIONS

D. Livant et al., "Invasion of Selectivity Permeable Sea Urchin Embryo Basement Membranes by Metastatic Tumor Cells, But Not By Their Normal Counterparts," *Cancer Research* 55:5085 (1995).

Bresalier et al., "The Laminin 1 Chain Ile–Lys–Val–Ala–Val (IKVAV)–Containing Peptide Promotes Liver Colonization by Human Colon Cancer Cells," *Cancer Research* 55:2476 (1995).

Eldred et al., "Orally Active Non–Peptide Fibrinogen Receptor (GpIIb/IIIa) Antagonists: Identification of 4–[4–[4–(Aminoiminomethyl) pheny1]–1–piperaziny1]–1–piperidineacetic Acid as a Long–Acting, Broad–Spectrum Antithrombotic Agent," *J. Med. Chem.*, 37:3882 (1994).

Ku et al., "Potent Non–Peptide Fibrinogen Receptor Antagonists Which Present An Alternative Pharmacophore," *J. Med. Chem.*, 38:9 (1995).

W.R. Pearson and D.J. Lipman, "Improved Tools For Biological Sequence Comparison," *Proc. Natl. Acad. Sci. (USA)*, 85:2444–2448 (1988).

D.J. Lipman and W.R. Pearson, "Rapid and Sensitive Protein Similarity Searches," *Science*, 227:1435–1441 (1985).

Douillard and Hoffman, "Basic Facts about Lymphocytes Hybridomas," *Compendium of Immunology vol. II*, ed. by Schwartz (1981).

G. Kohler and C. Milstein, "Continuous Cultures of Fused Cells Secreting Antibody of Predefined Specificity," *Nature*, 256:495–497 (1975).

G. Kohler and C. Milstein, "Derivation of Specific Antibody–Producing Tissue Culture and Tumor Lines By Cell Fusion," *European Journal of Immunology*, 6:511–519 (1976).

C.L. Reading, "Theory and Methods For Immunization in Culture and Monoclonal Antibody Production," *Journal of Immunological Methods*, 53:261–291 (1982).

T.K. Gartner et al., "The Tetrapeptide Analogue of the Cell Attachement Site of Fibronectin Inhibitis Platelet Aggregation and Fibrinogen Binding to Activated Platelets," *The Journal of Biological Chemistry*, 260:11891–11894 (1985).

N.S. Nicholson et al., "In Vitro and In Vivo Effects of a Peptide Mimetic (SC–47643) of RGD As An Antiplatelet and Antithrombotic Agent," *Thrombosis Research*, 62:567–578 (1995).

M. Nomizu et al., "Multimeric Forms of Tyr–Ile–Gly–Ser–Arg (YIGSR) Peptide Enhance the Inhibition of Tumor Growth and Metastasis," *Cancer Research*, 53:3459–3461 (1993).

I. Saiki et al., "Inhibition of the Metastasis of Murine Malignant Melanoma By Synthetic Polymeric Peptides Containing Core Sequences of Cell–Adhesive Molecules," *Cancer Research*, 49:3815–3822 (1989).

R.H. Wenger et al., "Cloning of cDNA Coding For Connective Tissue Activating Peptide III From a Human Platelet–Derived AgtII Expression Library," *Blood,* 73(6):1498–1503 (1992).

Aota et al; J. Biological Chem, vol. 269(4), (Oct. 7, 1994), pp. 24756–24761.

Kumar et al; Virchows Arch [Pathol Anat] (1984) vol. 405, pp. 95–111.

SEQUENCE LISTING ( 1 ) GENERAL INFORMATION:

( i i i ) NUMBER OF SEQUENCES: 86

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:1:

Pro   His   Ser   Arg   Asn
    1                              5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

Ile   Lys   Val   Ala   Val
    1                              5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: Not Relevant (D) TOPOLOGY: Not Relevant (ii) MOLECULE TYPE: peptide (xi) SEQUENCE DESCRIPTION: SEQ ID NO:3:

```
Pro His Ser Arg Asn Ser
1               5
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

```
Pro His Ser Arg Asn Ser Ile
1               5
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

```
Pro His Ser Arg Asn Ser Ile Thr
1               5
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

```
Pro His Ser Arg Asn Ser Ile Thr Leu
1               5
```

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:7:

```
Pro His Ser Arg Asn Ser Ile Thr Leu Thr
1               5                   10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: Not Relevant (D) TOPOLOGY: Not Relevant (ii) MOLECULE TYPE: peptide (xi) SEQUENCE DESCRIPTION: SEQ ID NO:8:

Pro His Ser Arg Asn Ser Ile Thr Leu Thr Asn
1               5                   10

(2) INFORMATION FOR SEQ ID NO:9:

(i) SEQUENCE CHARACTERISTICS:
    (A) LENGTH: 12 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:9:

Pro His Ser Arg Asn Ser Ile Thr Leu Thr Asn Leu
1               5                   10

(2) INFORMATION FOR SEQ ID NO:10:

(i) SEQUENCE CHARACTERISTICS:
    (A) LENGTH: 13 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:10:

Pro His Ser Arg Asn Ser Ile Thr Leu Thr Asn Leu Thr
1               5                   10

(2) INFORMATION FOR SEQ ID NO:11:

(i) SEQUENCE CHARACTERISTICS:
    (A) LENGTH: 14 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:11:

Pro His Ser Arg Asn Ser Ile Thr Leu Thr Asn Leu Thr Pro
1               5                   10

(2) INFORMATION FOR SEQ ID NO:12:

(i) SEQUENCE CHARACTERISTICS:
    (A) LENGTH: 15 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:12:

Pro His Ser Arg Asn Ser Ile Thr Leu Thr Asn Leu Thr Pro Gly
1               5                   10                  15

(2) INFORMATION FOR SEQ ID NO:13:

(i) SEQUENCE CHARACTERISTICS:
    (A) LENGTH: 18 amino acids
    (B) TYPE: amino acid
    (C) STRANDEDNESS: Not Relevant (D) TOPOLOGY: Not Relevant (ii) MOLECULE TYPE: peptide (xi) SEQUENCE DESCRIPTION: SEQ ID NO:13:

Pro Glu His Phe Ser Gly Arg Pro Arg Glu Asp Arg Val Pro His Ser
1               5                   10                  15
Arg Asn (2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:14:

Glu His Phe Ser Gly Arg Pro Arg Glu Asp Arg Val Pro His Ser Arg
1               5                   10                  15
Asn (2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:15:

His Phe Ser Gly Arg Pro Arg Glu Asp Arg Val Pro His Ser Arg Asn
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:16:

Phe Ser Gly Arg Pro Arg Glu Asp Arg Val Pro His Ser Arg Asn
1               5                   10                  15

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:17:

Ser Gly Arg Pro Arg Glu Asp Arg Val Pro His Ser Arg Asn
1               5                   10

(2) INFORMATION FOR SEQ ID NO:18:

( i ) SEQUENCE CHARACTERISTICS:
  ( A ) LENGTH: 13 amino acids
  ( B ) TYPE: amino acid
  ( C ) STRANDEDNESS: Not Relevant
  ( D ) TOPOLOGY: Not Relevant ( i i ) MOLECULE TYPE: peptide ( x i ) SEQUENCE DESCRIPTION: SEQ ID NO:18:

Gly Arg Pro Arg Glu Asp Arg Val Pro His Ser Arg Asn
1               5                       10

( 2 ) INFORMATION FOR SEQ ID NO:19:

( i ) SEQUENCE CHARACTERISTICS:
    ( A ) LENGTH: 12 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:19:

Arg Pro Arg Glu Asp Arg Val Pro His Ser Arg Asn
1               5                       10

( 2 ) INFORMATION FOR SEQ ID NO:20:

( i ) SEQUENCE CHARACTERISTICS:
    ( A ) LENGTH: 11 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:20:

Pro Arg Glu Asp Arg Val Pro His Ser Arg Asn
1               5                   10

( 2 ) INFORMATION FOR SEQ ID NO:21:

( i ) SEQUENCE CHARACTERISTICS:
    ( A ) LENGTH: 10 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:21:

Arg Glu Asp Arg Val Pro His Ser Arg Asn
1               5                   10

( 2 ) INFORMATION FOR SEQ ID NO:22:

( i ) SEQUENCE CHARACTERISTICS:
    ( A ) LENGTH: 9 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:22:

Glu Asp Arg Val Pro His Ser Arg Asn
1               5

( 2 ) INFORMATION FOR SEQ ID NO:23:

( i ) SEQUENCE CHARACTERISTICS:
    ( A ) LENGTH: 8 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:23:

Asp Arg Val Pro His Ser Arg Asn
1               5

( 2 ) INFORMATION FOR SEQ ID NO:24:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:24:

Arg Val Pro His Ser Arg Asn
1               5

( 2 ) INFORMATION FOR SEQ ID NO:25:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:25:

Val Pro His Ser Arg Asn
1               5

( 2 ) INFORMATION FOR SEQ ID NO:26:

( i ) SEQUENCE CHARACTERISTICS:
    ( A ) LENGTH: 28 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:26:

Pro Glu His Phe Ser Gly Arg Pro Arg Glu Asp Arg Val Pro His Ser
1               5                   10                  15

Arg Asn Ser Ile Thr Leu Thr Asn Leu Thr Pro Gly
            20                  25

( 2 ) INFORMATION FOR SEQ ID NO:27:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:27:

Pro Pro Ser Arg Asn
1               5

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:28:

His His Ser Arg Asn
1                  5

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:29:

His Pro Ser Arg Asn
1                  5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:30:

Pro His Thr Arg Asn
1                  5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:31:

His His Thr Arg Asn
1                  5

( 2 ) INFORMATION FOR SEQ ID NO:32:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:32:

His Pro Thr Arg Asn
1                  5

( 2 ) INFORMATION FOR SEQ ID NO:33:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:33:

Pro His Ser Asn Asn
    1                  5

( 2 ) INFORMATION FOR SEQ ID NO:34:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:34:

His His Ser Asn Asn
    1                  5

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:35:

His Pro Ser Asn Asn
    1                  5

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:36:

Pro His Thr Asn Asn
    1                  5

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:37:

His His Thr Asn Asn
    1                  5

( 2 ) INFORMATION FOR SEQ ID NO:38:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:38:

His  Pro  Thr  Asn  Asn
    1                           5

( 2 ) INFORMATION FOR SEQ ID NO:39:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:39:

Pro  His  Ser  Lys  Asn
    1                           5

( 2 ) INFORMATION FOR SEQ ID NO:40:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:40:

His  His  Ser  Lys  Asn
    1                           5

( 2 ) INFORMATION FOR SEQ ID NO:41:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:41:

His  Pro  Ser  Lys  Asn
    1                           5

( 2 ) INFORMATION FOR SEQ ID NO:42:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:42:

Pro  His  Thr  Lys  Asn
    1                           5

( 2 ) INFORMATION FOR SEQ ID NO:43:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:43:

```
His His Thr Lys Asn
1               5
```

( 2 ) INFORMATION FOR SEQ ID NO:44:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:44:

```
His Pro Thr Lys Asn
1               5
```

( 2 ) INFORMATION FOR SEQ ID NO:45:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:45:

```
Pro His Ser Arg Arg
1               5
```

( 2 ) INFORMATION FOR SEQ ID NO:46:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:46:

```
His His Ser Arg Arg
1               5
```

( 2 ) INFORMATION FOR SEQ ID NO:47:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:47:

```
His Pro Ser Arg Arg
1               5
```

( 2 ) INFORMATION FOR SEQ ID NO:48:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:48:

```
Pro  His  Thr  Arg  Arg
1                     5
```

( 2 ) INFORMATION FOR SEQ ID NO:49:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:49:

```
His  His  Thr  Arg  Arg
1                     5
```

( 2 ) INFORMATION FOR SEQ ID NO:50:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:50:

```
His  Pro  Thr  Arg  Arg
1                     5
```

( 2 ) INFORMATION FOR SEQ ID NO:51:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:51:

```
Pro  His  Ser  Asn  Arg
1                     5
```

( 2 ) INFORMATION FOR SEQ ID NO:52:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:52:

```
His  His  Ser  Asn  Arg
1                     5
```

( 2 ) INFORMATION FOR SEQ ID NO:53:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:53:

His  Pro  Ser  Asn  Arg
    1                       5

( 2 ) INFORMATION FOR SEQ ID NO:54:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:54:

Pro  His  Thr  Asn  Arg
    1                       5

( 2 ) INFORMATION FOR SEQ ID NO:55:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:55:

His  His  Thr  Asn  Arg
    1                       5

( 2 ) INFORMATION FOR SEQ ID NO:56:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:56:

His  Pro  Thr  Asn  Arg
    1                       5

( 2 ) INFORMATION FOR SEQ ID NO:57:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:57:

Pro  His  Ser  Lys  Arg
    1                       5

( 2 ) INFORMATION FOR SEQ ID NO:58:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:58:

```
His His Ser Lys Arg
1               5
```

( 2 ) INFORMATION FOR SEQ ID NO:59:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:59:

```
His Pro Ser Lys Arg
1               5
```

( 2 ) INFORMATION FOR SEQ ID NO:60:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:60:

```
Pro His Thr Lys Arg
1               5
```

( 2 ) INFORMATION FOR SEQ ID NO:61:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:61:

```
His His Thr Lys Arg
1               5
```

( 2 ) INFORMATION FOR SEQ ID NO:62:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:62:

```
His Pro Thr Lys Arg
1               5
```

( 2 ) INFORMATION FOR SEQ ID NO:63:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:63:

Pro His Ser Arg Lys
  1               5

( 2 ) INFORMATION FOR SEQ ID NO:64:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:64:

His His Ser Arg Lys
  1               5

( 2 ) INFORMATION FOR SEQ ID NO:65:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:65:

His Pro Ser Arg Lys
  1               5

( 2 ) INFORMATION FOR SEQ ID NO:66:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:66:

Pro His Thr Arg Lys
  1               5

( 2 ) INFORMATION FOR SEQ ID NO:67:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:67:

His His Thr Arg Lys
  1               5

( 2 ) INFORMATION FOR SEQ ID NO:68:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:68:

```
His  Pro  Thr  Arg  Lys
1                    5
```

( 2 ) INFORMATION FOR SEQ ID NO:69:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:69:

```
Pro  His  Ser  Asn  Lys
1                    5
```

( 2 ) INFORMATION FOR SEQ ID NO:70:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:70:

```
His  His  Ser  Asn  Lys
1                    5
```

( 2 ) INFORMATION FOR SEQ ID NO:71:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:71:

```
His  Pro  Ser  Asn  Lys
1                    5
```

( 2 ) INFORMATION FOR SEQ ID NO:72:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: Not Relevant ( i i ) MOLECULE TYPE: peptide ( x i ) SEQUENCE DESCRIPTION: SEQ ID NO:72:

```
Pro  His  Thr  Asn  Lys
1                    5
```

( 2 ) INFORMATION FOR SEQ ID NO:73:

( i ) SEQUENCE CHARACTERISTICS:
      ( A ) LENGTH: 5 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:73:

His His Thr Asn Lys
  1               5

( 2 ) INFORMATION FOR SEQ ID NO:74:

( i ) SEQUENCE CHARACTERISTICS:
      ( A ) LENGTH: 5 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:74:

His Pro Thr Asn Lys
  1               5

( 2 ) INFORMATION FOR SEQ ID NO:75:

( i ) SEQUENCE CHARACTERISTICS:
      ( A ) LENGTH: 5 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:75:

Pro His Ser Lys Lys
  1               5

( 2 ) INFORMATION FOR SEQ ID NO:76:

( i ) SEQUENCE CHARACTERISTICS:
      ( A ) LENGTH: 5 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:76:

His His Ser Lys Lys
  1               5

( 2 ) INFORMATION FOR SEQ ID NO:77:

( i ) SEQUENCE CHARACTERISTICS:
      ( A ) LENGTH: 5 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:77:

His Pro Ser Lys Lys
  1               5

( 2 ) INFORMATION FOR SEQ ID NO:78:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:78:

Pro His Thr Lys Lys
1                       5

( 2 ) INFORMATION FOR SEQ ID NO:79:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:79:

His His Thr Lys Lys
1                       5

( 2 ) INFORMATION FOR SEQ ID NO:80:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:80:

His Pro Thr Lys Lys
1                       5

( 2 ) INFORMATION FOR SEQ ID NO:81:

( i ) SEQUENCE CHARACTERISTICS:
        ( A ) LENGTH: 3 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:81:

Arg Gly Asp
1

( 2 ) INFORMATION FOR SEQ ID NO:82:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:82:

Pro His Ser Arg Asn
1                       5

(2) INFORMATION FOR SEQ ID NO:83:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:83:

Ile Lys Val Ala Val
    1               5

(2) INFORMATION FOR SEQ ID NO:84:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:84:

Gly Arg Gly Asp Ser Pro
    1               5

(2) INFORMATION FOR SEQ ID NO:85:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:85:

Gly Arg Gly Glu Ser Pro
    1               5

(2) INFORMATION FOR SEQ ID NO:86:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:86:

Pro His Ser Arg Asn Cys
    1               5

METHODS OF TESTING CANCER CELLS AND ANTICANCER DRUGS

FIELD OF THE INVENTION

The invention generally relates to the treatment of cancer, and, more specifically, to the testing of cancer cells for their ability to invade tissues and cause metastases, and to the identification and use of drugs to inhibit tumor invasion and growth.

BACKGROUND

The term "chemotherapy" simply means the treatment of disease with chemical substances. The father of chemotherapy, Paul Ehrlich, imagined the perfect chemotherapeutic as a "magic bullet;" such a compound would kill invading organisms without harming the host. This target specificity is sought in all types of chemotherapeutics, including anticancer agents.

However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman *The Pharmacological Basis of Therapeutics* (Pergamon Press, 8th Edition) (pp. 1209–1216).

Success with chemotherapeutics as anticancer agents has also been hampered by the phenomenon of multiple drug resistance, resistance to a wide range of structurally unrelated cytotoxic anticancer compounds. J. H. Gerlach et al., *Cancer Surveys*, 5:25–46 (1986). The underlying cause of progressive drug resistance may be due to a small population of drug-resistant cells within the tumor (e.g., mutant cells) at the time of diagnosis. J. H. Goldie and Andrew J. Coldman, *Cancer Research*, 44:3643–3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

Finally, the treatment of cancer has been hampered by the fact that there is considerable heterogeneity even within one type of cancer. Some cancers, for example, have the ability to invade tissues and display an aggressive course of growth characterized by metastases. These tumors generally are associated with a poor outcome for the patient. And yet, without a means of identifying such tumors and distinguishing such tumors from non-invasive cancer, the physician is at a loss to change and/or optimize therapy.

What is needed is a specific anticancer approach that is reliable for a wide variety of tumor types, and particularly suitable for invasive tumors. Importantly, the treatment must be effective with minimal host toxicity.

SUMMARY OF THE INVENTION

The invention generally relates to the treatment of cancer, and, more specifically, to the testing of cancer cells for their ability to invade tissues and cause metastases, and to the identification and use of drugs to inhibit tumor invasion and growth. The present invention provides A) an in vitro model for testing cancer cells and evaluating invasive potential, B) a screening assay for identifying drugs that inhibit tumor invasion, and C) chemotherapeutics for treating invasive tumors.

A variety of assay formats are contemplated for testing the invasive potential of cancer cells. In one embodiment, a portion of a patient's tumor is obtained (e.g., by biopsy) and placed in tissue culture on a fibronectin-free substrate. Thereafter, the response of the tumor cells to a fibronectin-derived peptide is assessed. Where the fibronectin-derived peptide induces invasion of the membrane, the tumor can be considered to have metastatic potential. Where there is no significant invasion of the membrane, the tumor can be considered (at that time) to be non-metastatic.

In one embodiment, the present invention contemplates a method of evaluating human cancer comprising: a) providing i) a human cancer patient, ii) a fibronectin-free substrate, and iii) one or more invasion-inducing agents; b) obtaining cancer cells from said patient; c) contacting said cells ex vivo with said fibronectin-free substrate and one or more invasion-inducing agents; and d) detecting cancer cell invasion of said substrate. Preferably the cancer cells are cultured in serum-free culture media so as to essentially avoid introducing complicating factors. In one embodiment, the invasion-inducing agent is a peptide, said peptide comprising the sequence PHSRN (SEQ ID No. 1).

While not limited to any mechanism, it is believed that cells exposed to invasion-inducing agents in this manner are potentially rendered capable of invading the substrate. Again, while not limited to any mechanism, it is believed that the invasion inducing agent comprising the sequence PHSRN (SEQ ID No. 1) binds to the $\alpha 5\beta 1$ receptor on the cancer cell and thereby induces invasion of the substrate. In this regard, the present invention provides a method of testing human cancer cells comprising: a) providing i) a human cancer patient, ii) a fibronectin-free substrate, and iii) one or more invasion-inducing agents; b) obtaining $\alpha 5\beta 1$ receptor-expressing cancer cells from said patient; c) culturing said cells in serum-free culture media on said substrate in the presence of said invasion-inducing agents; and d) detecting cancer cell invasion of said substrate.

As noted above, the present invention also contemplates a screening assay for identifying drugs that inhibit tumor invasion. The present invention contemplates a screening assay utilizing the binding activity of fibronectin-derived peptides. In one embodiment, an inducible tumor cell line is placed in tissue culture on a fibronectin-free substrate. Thereafter, as an inducible tumor cell line, the tumor will be induced (under ordinary conditions) by the fibronectin-derived peptide to invade the substrate. However, in this drug screening assay, candidate drug inhibitors are added to the tissue culture (this can be done individually or in mixtures). Where the inducible tumor cell is found to be inhibited from invading the substrate, a drug inhibitor is indicated.

It is not intended that the present invention be limited by the nature of the drugs screened in the screening assay of the present invention. A variety of drugs, including peptides, are contemplated.

Finally, the present invention contemplates chemotherapeutics for treating invasive tumors. In one embodiment, the present invention contemplates chemotherapeutics to antagonize the invasion-promoting activity of the plasma fibronectin PHSRN (SEQ ID No. 1) sequence on metastatic tumor cells. In another embodiment, the present invention contemplates anti-invasion antagonists to the IKVAV (SEQ ID No. 2) sequence of laminin.

The present invention further contemplates using antagonists before and/or after surgical removal of the primary tumor. In one embodiment, the method comprises administering a PHSRN (SEQ ID No. 1) antagonist as adjunct therapy with additional chemotherapeutics.

DEFINITIONS

Figure 1:
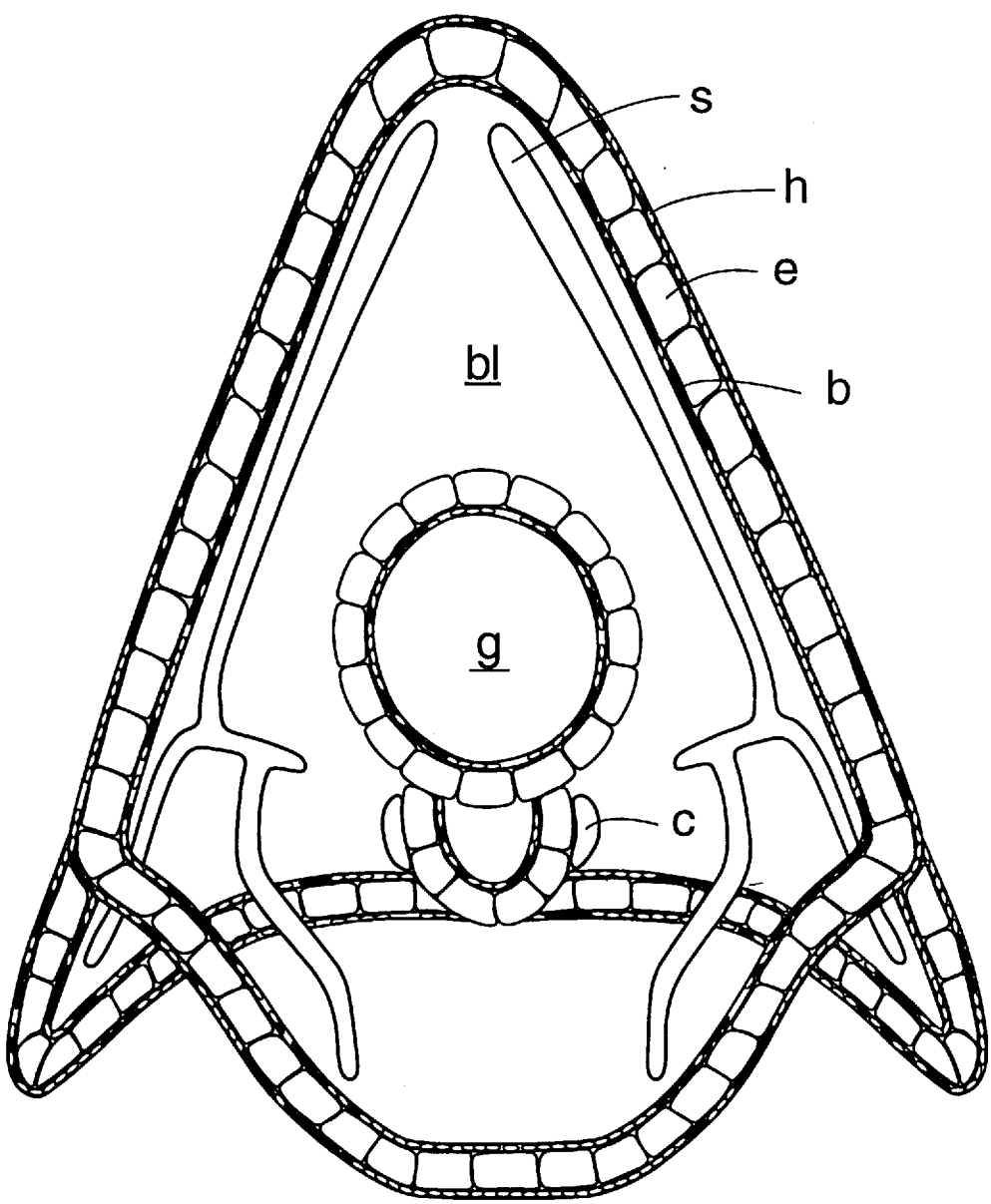
FIG. 1 schematically shows the one embodiment of the substrate used according to the present invention for testing tumor cells. The spatial relationship of the ectoderm of the *Strongylocentrotus purpuratus* embryo to its extracellular matrix and to blastocoelar structures are shown (s, spicules; h, hyalin layer; e, ectoderm; b, subectodermal basement membrane; bl, blastocoel; g, stomach of the primitive gut; c, coelomic pouches). The esophagus and intestine do not appear on the side of the embryo shown.

The term "drug" as used herein, refers to any medicinal substance used in humans or other animals. Encompassed within this definition are compound analogs, naturally occurring, synthetic and recombinant pharmaceuticals, hormones, antimicrobials, neurotransmitters, etc.

The term "inducing agent" refers to any compound or molecule which is capable of causing (directly or indirectly) the invasion of cells in a substrate. "Inducing agents" include, but are not limited to, PHSRN (SEQ ID No. 1) -containing peptides and related peptides (see below).

The term "receptors" refers to structures expressed by cells and which recognize binding molecules (e.g. ligands).

The term "antagonist" refers to molecules or compounds which inhibit the action of a "native" or "natural" compound (such as fibronectin). Antagonists may or may not be homologous to these natural compounds in respect to conformation, charge or other characteristics. Thus, antagonists may be recognized by the same or different receptors that are recognized by the natural compound.

The term "host cell" or "cell" refers to any cell which is used in any of the screening assays of the present invention. "Host cell" or "cell" also refers to any cell which either naturally expresses particular receptors of interest or is genetically altered so as to produce these normal or mutated receptors.

DESCRIPTION OF THE INVENTION

The invention generally relates to the treatment of cancer, and, more specifically, to the testing of cancer cells for their ability to invade tissues and cause metastases, and to the identification and use of drugs to inhibit tumor invasion and growth. As a prelude to metastasis, it is believed that cancer cells proteolytically alter basement membranes underlying epithelia or the endothelial linings of blood and lymphatic vessels, invade through the defects created by proteolysis, and enter the circulatory or lymphatic systems to colonize distant sites. During this process, the secretion of proteolytic enzymes is coupled with increased cellular motility and altered adhesion. After their colonization of distant sites, metastasizing tumor cells proliferate to establish metastatic nodules.

As noted above, chemotherapeutic agents are currently employed to reduce the unrestricted growth of cancer cells, either prior to surgical removal of the tumor (neoadjuvant therapy) or after surgery (adjuvant therapy). However, none of these methods has proved curative once metastasis has occurred. Since unrestricted invasive behavior is also a hallmark of metastatic tumor cells, methods for directly inhibiting tumor cell invasion and metastasis are needed.

A. Assays for Testing Tumor Invasion

Discovering how to inhibit the invasive behavior of tumor cells to intervene in the metastatic cascade first requires the development of assays with which to test tumor cell invasion in vitro. Two assay systems are contemplated for use in the method of the present invention to test the tumor cell invasion.

1. Fibronectin-depleted Substrates

In one assay system, the present invention contemplates using fibronectin-depleted substrates. These are substrates that originally contain fibronectin that are treated according to the methods of the present invention (see below) to remove fibronectin. It is not intended that the present invention be limited by the nature of the original subtrate; such fibronectin-containing substrates suitable for treatment and depletion include i) complex substrates containing a variety of extracellular proteins and ii) less complex substrates containing fibronectin along with one or two other proteins (e.g. collagen, laminin, etc.).

It is also not intended that the present invention be limited by the precise amount of fibronectin remaining after the substrate has been treated. In other words, while the methods of the present invention remove fibronectin, and in some embodiments, remove substantially all fibronectin, it is within the meaning of the term "fibronectin-depleted" substrate that a small amount of fibronectin remain in the substrate.

In one embodiment, the present invention contemplates using an extracellular matrix available commercially. For example, the present invention contemplates treating basement membrane matrices such as ECM GEL, a matrix from mouse sarcoma (commercially available from Sigma, St. Louis, Mo.). However, it is not intended that the present invention be limited by the particular fibronectin-containing substrate. For example, other commercially available susbtrates are contemplated, such as the commonly used substrate Matrigel (available from Becton Dickinson Labware, Catalog #40234); Matrigel can be treated appropriately according to the methods of the present invention so as to render it "fibronectin-depleted" (see below). Untreated Matrigel (and similar substrates) have been used to demonstrate the importance of proteases and mortality factors in the invasion and metastasis of many tumors. However, these invasion substrates are not available as serum-free substrates; thus, the regulation of tumor cell invasive behavior by serum components, such as plasma fibronectin, is a complicating factor with untreated Matrigel.

Consequently, the present invention contemplates a fibronectin-free substrate. In this embodiment, Matrigel is treated so that it is substantially fibronectin-free. The preparation of fibronectin-free Matrigel involves "panning" the Matrigel substrate on gelatin as well as "panning" the substrate on anti-fibronectin antibody (anti-human fibronectin IgG is available commercially, such as antibody from Promega Corporation, Madison, Wis.).

2. Naturally Occurring Fibronectin-free Substrates

In another embodiment, the present invention contemplates substrates that are naturally free of fibronectin; such a source provides, for example, basement membranes permeable to select types of normally invasive cells, such membranes being naturally serum-free. In one embodiment, the present invention contemplates sea urchins as a source of such membranes. In this regard, the ectoderm of sea urchin embryos is one cell thick, and secretes an underlying basement membrane (see FIG. 1) very similar to that of mammals. These embryos contain no circulatory or lymphatic systems; and thus, their basement membranes are serum-free. In embryos, the subectodermal basement membrane functions simultaneously as a migration substrate for several, specific mesenchymal cell types while it functions as an invasion substrate for others. Sea urchin embryo basement membranes (SU-ECM) can be prepared by mild detergent treatment as described in D. Livant et al., *Cancer Research* 55:5085 (1995) and described in the Experimental section below.

Regardless of which of the two types of substrates are employed, the invasion substrates of the present invention are easy to prepare and give rapid, highly consistent results with a variety of cells, including a) cell lines from i) primary and metastatic tumors, and ii) normal epithelial tissues, as well as b) cells from primary tissue samples of both tumors, their surrounding normal tissues, and neonatal melanocytes, fibroblasts, and keratinocytes from circumcised tissue.

In one embodiment, the present invention contemplates a method of evaluating human cancer comprising: a) providing i) a human cancer patient (such as a patient with breast cancer or prostate cancer), ii) a fibronectin-free substrate (for example, a fibronectin-depleted substrate) and iii) one or more invasion-inducing agents (discussed below); b) obtaining cancer cells from said patient (such as from a biopsy); c) contacting said cells ex vivo (i.e. outside the body) with said fibronectin-free substrate and said one or more invasion-inducing agents; and d) measuring the extent of cancer cell invasion of said substrate. Preferably the cancer cells are cultured in serum-free culture media so as to avoid introducing complicating factors.

3. Inducing Agents

It is not intended that the present invention be limited by the nature of the agent that causes or induces cells to invade the fibronectin-free substrates of the present invention. Such agents can be identified functionally by simply adding them to the cell culture and measuring the extent of invasion.

In one embodiment, the invasion-inducing agent comprises a peptide derived from fibronectin. In a preferred embodiment, said peptide comprises the sequence PHSRN (SEQ ID No. 1). Of course, the peptide may be larger than five amino acids; indeed, the peptide fragment of fibronectin may contain hundreds of additional residues (e.g. five hundred amino acids). One such larger peptide is set forth in U.S. Pat. No. 5,492,890 (hereby incorporated by reference). In one embodiment, the PHSRN-containing peptide is less than one hundred amino acids in length and lacks the RGD sequence characteristic of fibronectin. A variety of PHSRN (SEQ ID No. 1)-containing peptides are contemplated, including the PHSRN (SEQ ID No. 1) peptide itself and related peptides where additional amino acids are added to the carboxy terminus, including (but not limited to) peptides comprising the sequence: 1) PHSRN (SEQ ID No. 1), 2) PHSRNS (SEQ ID No. 3), 3) PHSRNSI (SEQ ID No. 4), 4) PHSRNSIT (SEQ ID No. 5), 5) PHSRNSITL (SEQ ID No. 6), 6) PHSRNSITLT (SEQ ID No. 7), 7) PHSRNSITLTN (SEQ ID No. 8), 8) PHSRNSITLTNL (SEQ ID No. 9), 9) PHSRNSITLTNLT (SEQ ID No. 10), 10) PHSRNSITLTNLTP (SEQ ID No. 11), and 11) PHSRNSITLTNLTPG (SEQ ID No. 12). Alternatively, PHSRN (SEQ ID No. 1)-containing peptides are contemplated where amino acids are added to the amino terminus, including (but not limited to) peptides comprising the sequence: 1) PEHFSGRPREDRVPHSRN (SEQ ID No. 13), 2) EHFSGRPREDRVPHSRN (SEQ ID No. 14), 3) HFSGRPREDRVPHSRN (SEQ ID No. 15), 4) FSGRPREDRVPHSRN (SEQ ID No. 16), 5) SGRPREDRVPHSRN (SEQ ID No. 17), 6) GRPREDRVPHSRN (SEQ ID No. 18), 7) RPREDRVPHSRN (SEQ ID No. 19), 8) PREDRVPHSRN (SEQ ID No. 20), 9) REDRVPHSRN (SEQ ID No. 21), 10) EDRVPHSRN (SEQ ID No. 22), 11) DRVPHSRN (SEQ ID No. 23), 12) RVPHSRN (SEQ ID No. 24), and 13) VPHSRN (SEQ ID No. 25). Finally, the present invention contemplates PHSRN (SEQ ID No. 1)-containing peptides where amino acids are added to both the amino and carboxy termini, including (but not limited to) peptides comprising the sequence PEHFSGRPREDRVPHSRNSITLTNLTPG (SEQ ID No. 26), as well as peptides comprising portions or fragments of the PHSRN-containing sequence PEHFSGRPREDRVPHSRNSITLTNLTPG (SEQ ID No. 26).

Peptides containing variations on the PHSRN (SEQ ID No. 1) motif are contemplated. For example, the present invention also contemplates PPSRN (SEQ ID No. 27)-containing peptides for use in the above-named assays. Such peptides may vary in length in the manner described above for PHSRN (SEQ ID No. 1)-containing peptides. Alternatively, PPSRN (SEQ ID No. 27) may be used as a peptide of five amino acids.

Similarly, peptides comprising the sequence -HHSRN (SEQ ID No. 28)-, -HPSRN (SEQ ID No. 29)-, -PHTRN (SEQ ID No. 30)-, -HHTRN (SEQ ID No. 31)-, -HPTRN (SEQ ID No. 32)-, -PHSNN (SEQ ID No. 33)-, -HHSNN (SEQ ID No. 34)-, -HPSNN (SEQ ID No. 35)-, -PHTNN (SEQ ID No. 36)-, -HHTNN (SEQ ID No. 37)-, -HPTNN (SEQ ID No. 38)-, -PHSKN (SEQ ID No. 39)-, -HHSKN (SEQ ID No. 40)-, -HPSKN (SEQ ID No. 41)-, -PHTKN (SEQ ID No. 42)-, -HHTKN (SEQ ID No. 43)-, -HPTKN (SEQ ID No. 44)-, -PHSRR (SEQ ID No. 45)-, -HHSRR (SEQ ID No. 46)-, -HPSRR (SEQ ID No. 47)-, -PHTRR (SEQ ID No. 48)-, -HHTRR (SEQ ID No. 49)-, -HPTRR (SEQ ID No. 50)-, -PHSNR (SEQ ID No. 51)-, -HHSNR (SEQ ID No. 52)-, -HPSNR (SEQ ID No. 53)-, -PHTNR (SEQ ID No. 54)-, -HHTNR (SEQ ID No. 55)-, -HPTNR (SEQ ID No. 56)-, -PHSKR (SEQ ID No. 57)-, -HHSKR (SEQ ID No. 58)-, -HPSKR (SEQ ID No. 59)-, -PHTKR (SEQ ID No. 60)-, -HHTKR (SEQ ID No. 61)-, -HPTKR-, -PHSRK-, -HHSRK-, -HPSRK-, -PHTRK-, -HHTRK-, -HPTRK-, -PHSNK-, -HHSNK-, -HPSNK-, -PHTNK-, -HHTNK-, -HPTNK-, -PHSKK-, -HHSKK-, -HPSKK-, -PHTKK-, -HHTKK-, or -HPTKK- are contemplated by the present invention. Such peptides can be used as five amino acid peptides or can be part of a longer peptide (in the manner set forth above for PHSRN-containing peptides).

While not limited to any mechanism, it is believed that cells exposed to invasion-inducing agents in this manner are potentially rendered capable of invading the substrate. Again, while not limited to any mechanism, it is believed that the invasion inducing agent comprising the sequence PHSRN binds to the α5β1 receptor on the cancer cell and thereby induces invasion of the substrate. In this regard, the present invention provides a method of treating cells comprising: a) providing i) cells expressing the α5β1 receptor, ii) a fibronectin-free substrate, and iii) one or more invasion-inducing agents; b) culturing said cells in serum-free culture media on said substrate in the presence of said invasion-inducing agents; and d) measuring the extent of cell invasion of said substrate. In one embodiment, the cells are human fibroblasts. In another embodiment, the cells are human cancer cells.

B. Drug Screening Assays

As noted above, the present invention also contemplates a screening assay for identifying drugs that inhibit tumor invasion. The present invention contemplates a screening assay utilizing the binding activity of fibronectin-derived peptides, including but not limited to the above-described peptides. In one embodiment, an inducible tumor cell line is placed in tissue culture on a fibronectin-free substrate. The tumor cells will be induced (under ordinary conditions) by the fibronectin-derived peptide to invade the substrate. However, in this drug screening assay, candidate drug inhibitors are added to the tissue culture (this can be done individually or in mixtures). Where the inducible tumor cell is found to be inhibited from invading the substrate, a drug inhibitor is indicated.

It is not intended that the present invention be limited by the nature of the drugs screened in the screening assay of the present invention. A variety of drugs, including peptides, are contemplated.

It is also not intended that the present invention be limited by the particular tumor cells used for drug testing. A variety of tumor cells (for both positive and negative controls) are contemplated (including but not limited to the cells set forth in Table 1 below).

C. Invasion-Inducing Agents and Antagonists

While an understanding of the mechanisms involved in metastatic cancer is not necessary to the successful practice of the present invention, it is believed that tumor cell invasion of basement membranes occurs at several points in the metastatic cascade; (1) when epithelial tumor cells (such as those of breast and prostate cancers) leave the epithelium and enter the stroma, (2) when tumor cells enter the circulatory

TABLE 1

Designation And Origin Of Human Cell Lines And Strains[1]

| ORIGIN | CELL LINES OR STRAINS |
|---|---|
| Colonic carcinoma | SW1116, HCT116, SKCO-1, HT-29, KM12C, KM12SM, KM12L4, SW480 |
| Pancreatic carcinoma | BxPC-3, AsPC-1, Capan-2, MIA PaCa-2, Hs766T |
| Colon adenoma | VaCo 235 |
| Lung carcinoma | A549 |
| Prostate carcinoma | PC-3, DU-145 |
| Breast carcinoma | 009P, 013T |
| Lymphoma | Daudi, Raji |
| Breast epithelium | 006FA |
| Diploid fibroblast | HCS (human corneal stroma), MRC-5 |

[1]The SW1116, HT-29, SW480, Raji lymphoblastoid cells, and the pancreatic lines are obtained from the American Type Culture Collection.

or lymphatic systems, and (3) when tumor cells leave the circulatory or lymphatic systems to invade distant sites. Thus, intervention in the induction of tumor cell invasiveness by using a PHSRN antagonist to block tumor cell receptors for this sequence is contemplated as a method for decreasing the rate of metastasis.

One advantage of this strategy is that leukocytes are the only normal cells known to invade tissues to carry out their functions, and relatively few leukocytes are invasive at a given time. Thus, relatively small doses of an anti-invasion antagonist which blocks the binding of PHSRN to its receptor are required. Also, other than some immunodepression, there should be relatively few side effects associated with anti-metastatic treatment using compounds designed to block the induction of invasion. The lack of debilitating side effects expected from anti-invasive therapy means that using it in combination with anti-proliferative agents would be uncomplicated, and that it could be used prior to surgery or even prophylactically to block tumor cell invasion and metastasis.

The IKVAV sequence of laminin, a prevalent insoluble protein of the extracellular matrix, is known to stimulate liver colonization by metastatic human colon cancer cells in athymic mice [see Bresalier et al., *Cancer Research* 55:2476 (1995)]. The present invention contemplates applying the strategy of developing anti-invasion antagonists to the IKVAV sequence of laminin.

1. Designing Mimetics

Compounds mimicking the necessary conformation for recognition and docking to the receptor binding to the peptides of the present invention are contemplated as within the scope of this invention. For example, mimetics of PHSRN peptides are contemplated. A variety of designs for such mimetics are possible. For example, cyclic PHSRN-containing peptides, in which the necessary conformation for binding is stabilized by nonpeptides, are specifically contemplated. U.S. Pat. No. 5,192,746 to Lobl, et al, U.S. Pat. No. 5,169,862 to Burke, Jr., et al, U.S. Pat. No. 5,539,085 to Bischoff, et al, U.S. Pat. No. 5,576,423 to Aversa, et al, U.S. Pat. No. 5,051,448 to Shashoua, and U.S. Pat. No. 5,559,103 to Gaeta, et al, all hereby incorporated by reference, describe multiple methods for creating such compounds.

Synthesis of nonpeptide compounds that mimic peptide sequences is also known in the art. Eldred, et al, (*J. Med. Chem.* 37:3882 (1994)) describe nonpeptide antagonists that mimic the Arg-Gly-Asp sequence. Likewise, Ku, et al, (*J. Med. Chem.* 38:9 (1995)) give further elucidation of the synthesis of a series of such compounds. Such nonpeptide compounds that mimic PHSRN peptides are specifically contemplated by the present invention.

The present invention also contemplates synthetic mimicking compounds that are multimeric compounds that repeat the relevant peptide sequence. In one embodiment of the present invention, it is contemplated that the relevant peptide sequence is Pro-His-Ser-Arg-Asn; in another embodiment, the relevant peptide sequence is Ile-Lys-Val-Ala-Val. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the (α-amino group of the component containing the activated carboxyl group can be blocked with a tertbutyloxycarbonyl group. This protecting group can be subsequently removed by exposing the peptide to dilute acid, which leaves peptide bonds intact. With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the above-described PHSRN-containing peptides. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, Science, 227:1435–1441 (1985). In the present invention, synthetic polypeptides useful in tumor therapy and in blocking invasion are those peptides with statistically significant sequence homology and similarity (Z value of Lipman and Pearson algorithm in Monte Carlo analysis exceeding 6).

2. Antibody Inhibitors

The present invention contemplates all types of inhibitors of tumor invasion for use in both the assays and for therapeutic use. In one embodiment, the present invention contemplates antibody inhibitors. The antibodies may be monoclonal or polyclonal. It is within the scope of this invention to include any second antibodies (monoclonal or polyclonal) directed to the first antibodies discussed above. Both the first and second antibodies may be used in the detection assays or a first antibody may be used with a commercially available anti-immunoglobulin antibody. An antibody as contemplated herein includes any antibody specific to any region of a peptide involved in the induction of tumor cell invasion. For example, the present invention contemplates antibodies reactive with PHSRN peptides (as well as the related peptides set forth above).

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of the purified enzyme or protein, or antigenic parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the enzyme or protein or antigenic parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen of lymph nodes of sensitized animals in a sterile fashion and carrying out fusion. Alternatively, lymphocytes can be stimulated or immunized in vitro, as described, for example, in Reading, *Journal of Immunological Methods* 53: 261–291, 1982.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine 1×10-4M, aminopterin 1×10-5M, and thymidine 3×10-5M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators.

Most of the common methods are sufficiently sensitive for use in the range of antibody concentrations secreted during hybrid growth.

Cloning of hybrids can be carried out after 21–23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

A wide range of immunoassay techniques are available for evaluating the antibodies of the present invention as can be seen by reference to U.S. Pat. Nos. 4,016,043; 4,424,279 and 4,018,653, hereby incorporated by reference. This, of course, includes both single-site and two-site, or "sandwich", assays of the non-competitive types, as well as in the traditional competitive binding assays.

3. Administering Chemotherapeutics

It is contemplated that the antagonists of the present invention (such as the PHSRN antagonists) can be administered systemically or locally to inhibit tumor cell invasion in cancer patients with locally advanced or metastatic cancers. They can be administered intravenously, intrathecally, intraperitoneally as well as orally. PHSRN antagonists can be administered alone or in combination with antiproliferative drugs in a neoadjuvant setting to reduce the metastatic load in the patient prior to surgery; or they can be administered after surgery. Since PHSRN antagonists may depress wound healing (because the PHSRN sequence also elicits fibroblast invasion as described below), it may be necessary to use PHSRN antagonists some time after surgery to remove the tumor.

Since few cells in the body must invade in order to function, PHSRN antagonists administered systemically are not likely to cause the debilitating side effects of cytotoxic chemotherapeutic agents. However, since they suppress invasion, they are likely to cause some immunodepression. Even so, at the appropriate dosage, PSHRN antagonists may be administered prophylactically. In any case, it is contemplated that they may be administered in combination with cytotoxic agents. The simultaneous selection against the two fatal attributes of metastatic cells, unrestricted proliferation and invasion, is contemplated as a very powerful therapeutic strategy.

Where combinations are contemplated, it is not intended that the present invention be limited by the particular nature of the combination. The present invention contemplates combinations as simple mixtures as well as chemical hybrids. An example of the latter is where the antagonist is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The antagonists of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

Wound Healing

As noted above, it is contemplated that PHSRN antagonists may depress wound healing. This expectation is based on the discovery that PHSRN-containing peptides promote wound healing.

In this regard, it should be noted that the therapy of wounds, particularly those which are made difficult to heal by disease, has been attempted with a variety of purified growth factors or cytokines because these molecules can induce cellular proliferation or increase the motility of cells in wounds. Thus, if presented in the correct form and location at the right time, growth factors may greatly accelerate or enhance the healing of wounds by stimulating the growth of new tissue. Given the complexity and clinical variability of wounds, an obvious difficulty with the application of specific, purified growth factors or cytokines to wounded tissue, alone or in combination, is that their forms or specific distributions in the wound may not support their normal activities. Instead, the effectiveness of growth factors and cytokines in promoting the healing of wounded tissue may depend on their secretion by fibroblasts or macrophages.

The present invention contemplates a more effective approach; this approach involves methods that stimulate the invasion of the wound by the cells which synthesize the growth factors and cytokines active in stimulating wound repair, especially monocytes, macrophages, and fibroblasts.

This strategy allows the cells in their normal in vivo setting to secrete the active factors. This approach has a number of advantages: (1) the temporal and spatial distributions of the factors are likely to be optimal because the normally active cells in their correct settings are secreting them; (2) all the appropriate factors are likely to be present in their active forms, irrespective of whether they have been identified or cloned; (3) the sequential effects of the factors in recruiting subsequent waves of cells involved in the healing process to the wound site are likely to be enhanced by the presence of more initiating cells in the wound.

The present invention is based on the discovery that the pure PHSRN peptide or purified plasma fibronectin fragments containing it, and lacking the α4β1 integrin binding site in the IIICS region, are sufficient to stimulate fibroblast invasion of basement membranes in vitro under serum-free conditions, while intact plasma fibronectin fails to stimulate fibroblast invasion. This suggests that this peptide, or forms of it not subject to rapid proteolysis, may have similar effects on fibroblasts and monocytes/macrophages in vivo. Recruitment of fibroblasts or monocytes/macrophages whose paracrine, regulatory effects on a variety of neighboring cells are required for the early stages of wound healing is contemplated as a highly efficient and effective way to stimulate the cascade of regulatory interactions involved in wound healing because these cells will secrete the active factors or cytokines in the correct temporal sequences and spatial locations to ensure their optimal activities. The use of the PHSRN peptide or structurally related molecules according to the present invention is to stimulate the entry of cells such as fibroblasts and monocyte/macrophages into the provisional matrix of a wound, so that the entering cells themselves secrete the factors and cytokines active in inducing or potentiating wound healing.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); nm (nanometers); °C. (degrees Centigrade); mAb (monoclonal antibody); MW (molecular weight); PBS (phophate buffered saline); U (units); d(days).

EXAMPLE 1

Production of Fibronectin-free Substrates

This example describes a purification approach for removal of plasma fibronectin (and/or cellular fibronectin) from a substrate (Matrigel). In this example, removal was attempted by affinity chromatography over Gelatin-Sepharose (a technique which can be used to remove plasma fibronectin from fetal calf serum).

The Gelatin-Sepharose beeds were obtained from Pharmacia (Catalog# 17-0956–01). Two Kontes columns were set up with about 2 mls of Gelatin-Sepharose beeads at 4 C. to prevent gelling of the Matrigel. The columns were then rised with about 10 column volumes of PBS to remove the preservative from the beads. The columns were drained to the top of the beads; then Matrigel was carefully added to the column. Once the Matrigel had entered the column, PBS was added to the top of the column. The Matrigel which was passed over the first column was collected and passed over the second column. The fibronectin-depleted Matrigel collected from the second solumn was plated on 48-well plates (150 $\mu$l/well), sterilized under a UV light for 10 minutes and incubated at 37 C. overnight. The Matrigel treated in this manner failed to form a gel at 37 C.

EXAMPLE 2

Production of Fibronectin-free Substrates

This example describes a purification approach for removal of plasma fibronectin (and/or cellular fibronectin) from a substrate (Matrigel). In this example, removal was attempted by successive panning on gelatin. Eight wells of 24-well plate were coated with a 2% gelatin solution (the gelatin was obtained from Becton Dickinson Labware, Catalog #11868). The wells were filled with the gelatin solution which had been heated to 50 C. and incubated for 3 minutes. Then the solution was removed and the wells were allowed to air dry. Following drying, the wells were thoroughly rised with hhH2O followed by two rinses with PBS. The plates were again allowed to dry; thereafter they were stored at –20 C. until use. Matrigel was thawed on ice and then added to one of the wells of a gelatin-coated plate (between 800 $\mu$l and 1 ml of Matrigel was added to a well of a 24-well plate). The plate was placed in a bucket of ice in a 4 C. room on an orbital shaker where the Matrigel was incubated in the well for two hours (although overnight incubation can be used). Following the incubation, the Matrigel was moved from the first well to a second well and then incubated for two hours under the same conditions. This process was repeated until the Matrigel had been incubated on all eight wells of the gelatin-coated plate.

Following the depletion of the Matrigel, it was collected in Eppendorf tubes. It was then plated on a 48-well plate 150 $\mu$l/well), sterilized under a UV light for 10 minutes and incubated at 37 C. overnight. The Matrigel formed as gel and the following day, cells were added to each well.

EXAMPLE 3

Production of Fibronectin-free Substrates

This example describes a purification approach for removal of plasma fibronectin (and/or cellular fibronectin) from a substrate (Matrigel). In this example, removal was attempted by gelatin panning followed by antibody panning.
Anti-fibronectin Antibody-coated Wells Wells of a 24-well plate were coated with an anti-fibronectin antibody. A mouse monoclonal antibody to human fibronectin was obtained from Oncogene Science (Catalog #CP13). Each well was incubated with 1 ml of antibody at a concentration of 30 $\mu$l/ml for 2 hours at room temperature. Each well was then incubated with a solution of 3% BSA in PBS for 2 hours at room temperature. Following the two incubation periods, the wells were thoroughly washed with PBS and stored at –20 C. until use.
Depleting Matrigel of Fibronectin Matrigel was panned over eight gelatin-coated wells (as described above in Example 2) to remove most of the fibronectin and its fragments. Thereafter, the Matrigel was placed in the antibody-coated wells to remove any remaining fragments of fibronectin which contain the cell-binding domain but not the gelatin-binding domain. The Matrigel was incubated in an ice bucket on an orbital shaker at 4 C.

for 2 hours. Once the Matrigel was depleted, it was collected in Eppendorf tubes. The fironectin-deplted Matrigel was plated on a 48-well plate (150 μl/well), sterilized under a UV light for 10 minutes and incubated at 37 C. overnight. The Matrigel formed a gel and the following day, cells were added to the wells.

EXAMPLE 4

Inducing Invasive Behavior Of Tumor Cells

In this example, the role of plasma fibronectin in inducing the invasive behaviors of metastatic breast and prostate cancer cells is demonstrated. Human breast carcinoma cell lines SUM 52 PE and SUM 44 PE were originally cultured from the pleural effusions of patents with metastatic breast cancer; and SUM 102 was cultured from a primary, microinvasive breast carcinoma. The DU 145 metastatic human prostate cancer cell line was originally cultured from a brain metastasis. These cells express $\alpha 3\beta 1$ which has been shown to repress metalloproteinase transcription upon binding the connecting segment of plasma Fn. These cell lines can all be cultured under serum-free conditions; thus they are ideal for use in serum-free invasion assays on SU-ECM.

Adult *Strongylocentrotus purpuratus* sea urchins were obtained from Pacific BioMarine, and their embryos were cultured to the early pluteus stage in artificial sea water at 15° C. SU-ECM were prepared from them by mild detergent treatment and strerilized by dilution in the appropriate media.

Cells were harvested by rinsing in Hanks' balanced salt solution, followed by brief treatment with 0.25% trypsin, 0.02% EDTA, and pelleting and resuspension in the appropriate medium with or without 5% FCS at a density of about 50,000 cells per ml. When appropriate, purified bovine plasma fibronectin (Sigma), or GRGDSP or GRGESP peptides (Gibco BRL) were added to the resuspended cells prior to placement of the cells on SU-ECM. In each well of a plate used for an invasion assay, SU-ECM were placed in 0.5 ml of the appropriate medium, and 0.5ml of the resuspended cells deropped on their exterior surfaces. Invasion assays were incubated 1 to 16 hours prior to assay. If some circumstances, invasion assays were fixed in phosphate-buffered saline (PBS) with 2% formaldehyde for 5 minutes at room temperature, then rinsed into PBS.

Invasion assays were coded and scored blindly by microscopic examination under phase contrast at 200- and 400-fold magnification. Each cell contacting an SU-ECM was scored for its position relative to the exterior or interior surfaces. A cell was judged to have invaded if it was located on an interior surface below the focal plane passing through the upper surface of the SU-ECM, but above the focal plane passing through its lower surface. The minimum viability of the cells in each assay was always ascertained at the time of assay by determining the fraction of spread, adherent cells on the bottom of each well scored.

An invasion frequency is defined as the fraction of cells in contact with basement membranes which were located in their interiors at the time of assay. Thus, an invasion frequency of 1 denotes invasion by 100% of the cells in contact with basement membranes. Invasion frequencies were determined multiple times for each cell type assayed. For each type of cell assayed the mean and standard deviation of the invasion frequencies were calculated.

The invasion-inducing sequences of plasma fibronectin was mapped to a peptide sequence 5 amino acids long, the PHSRN peptide, for both metastatic breast and prostate cancer cells. Since the PHSRN sequence is present in plasma fibronectin, a significant component of serum, eliciting the regulatory role of this sequence was only possible because of the availability of a serum-free in vitro invasion substrate. It should be noted that neonatal, human fibroblasts are also induced with the PHSRN peptide to invade serum-free SU-ECM. Although fibroblasts do not invade SU-ECM in the presence of serum, the 120 kDa fragment of plasma fibronectin containing the PHSRN sequence can induce fibroblast invasion equally well in the presence of serum or in its absence.

When taken together, the results of experiments showing that the PHSRN sequence of plasma fibronectin induces the invasive behaviors of both metastatic breast and prostate cancer cells, as well as that of normal fibroblasts suggest the intriguing possibility that the invasive behavior associated with tumor cell metastasis may result from defects in the regulation of the normal invasive behaviors associated with wound healing.

EXAMPLE 5

Testing Tumor Cells On Fibronectin-Depleted Substrates

Figure 2:
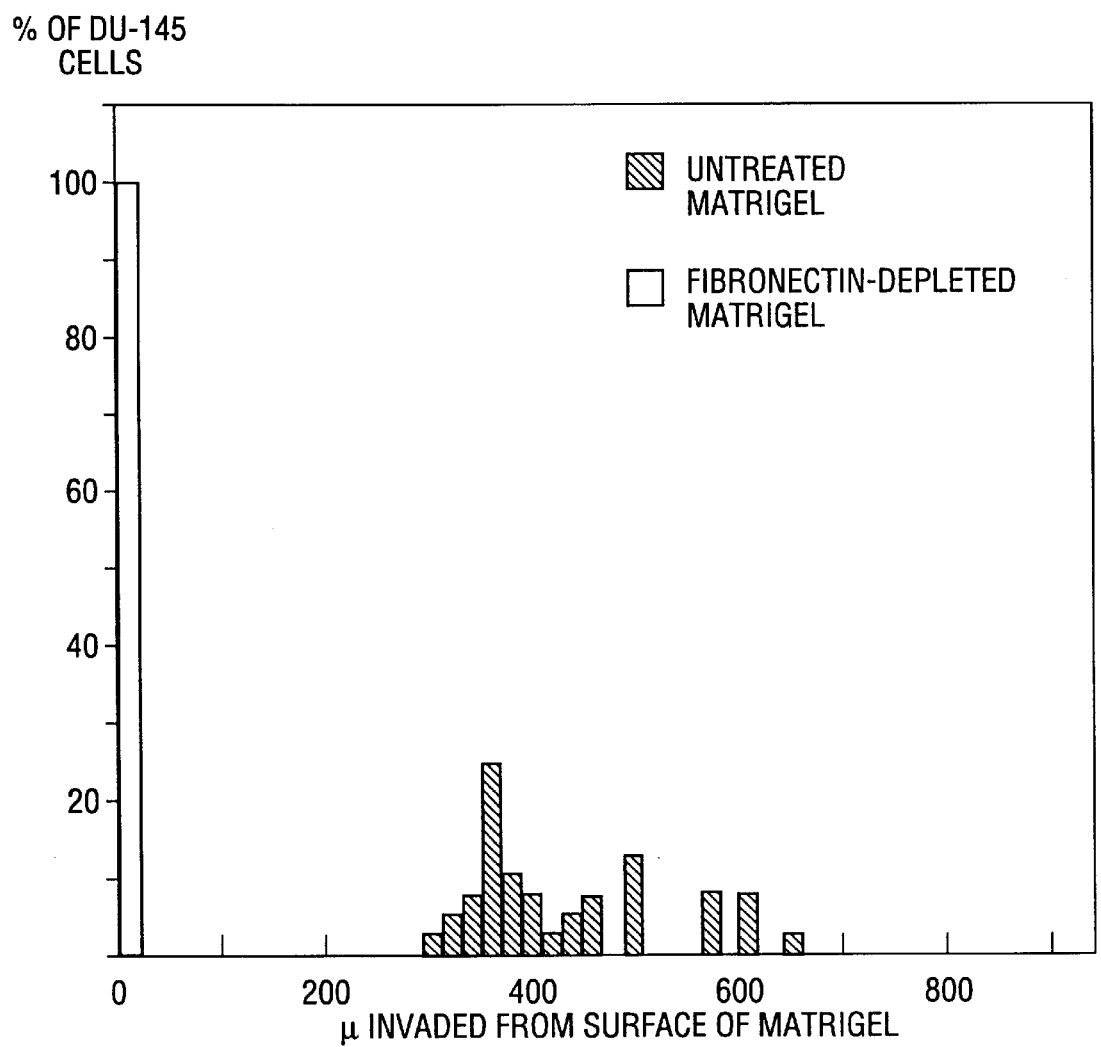
FIG. 2 is a graph showing the results of the testing of tumor cells on fibronectin-containing substrates and fibronectin-depleted substrates in vitro without the use of the invasion-inducing agents of the present invention.

This example describes an approach to test cancer cells in vitro on substrates with and without invasion-inducing agents. The depleted preparation of Matrigel (see Example 2, above) and untreated Matrigel were used to test DU-145 metastatic prostate cancer cells. When plated on the depleted medium, the cancer cells failed to invade the matrix (see FIG. 2). Indeed, it was evident that these cells were sitting on the surface of the depleted Matrigel because the Matrigel surface was slightly tilted; this was visible through the microscope as a gradual progressive, uniform change in the focal plane for the monolayer of DU-145 cells.

Figure 3:
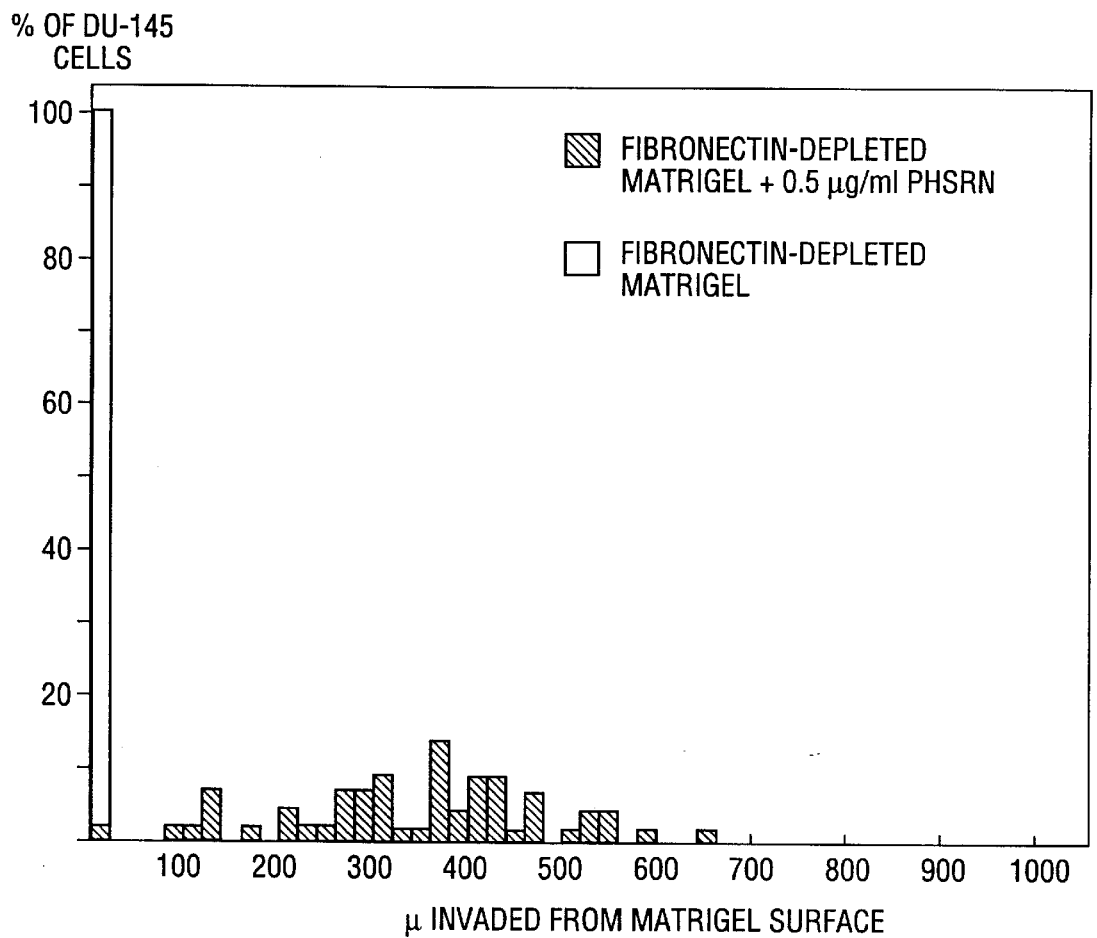
FIG. 3 is a graph showing the results of the testing of tumor cells on fibronectin-depleted substrates in vitro with and without invasion-inducing agents according one embodiment of the method of the present invention.

The addition of 0.5 μl/ml of the PHSRN peptide to the depleted Matrigel was sufficient to restore the full DU-145 invasiveness (see FIG. 3). Clearly, gelatin panning removes fibronectin such that cancer cells are unable to invade. Since the addition of PHSRN peptide in solution fully restores the DU-145 invasive phenotype, blocking the effect of PHSRN is an effective strategy for therapeutic intervention in tumor cell invasion and metastasis.

EXAMPLE 6

Improving Gelatin Depletion as Measured by Fibroblast Invasiveness

Figure 4:
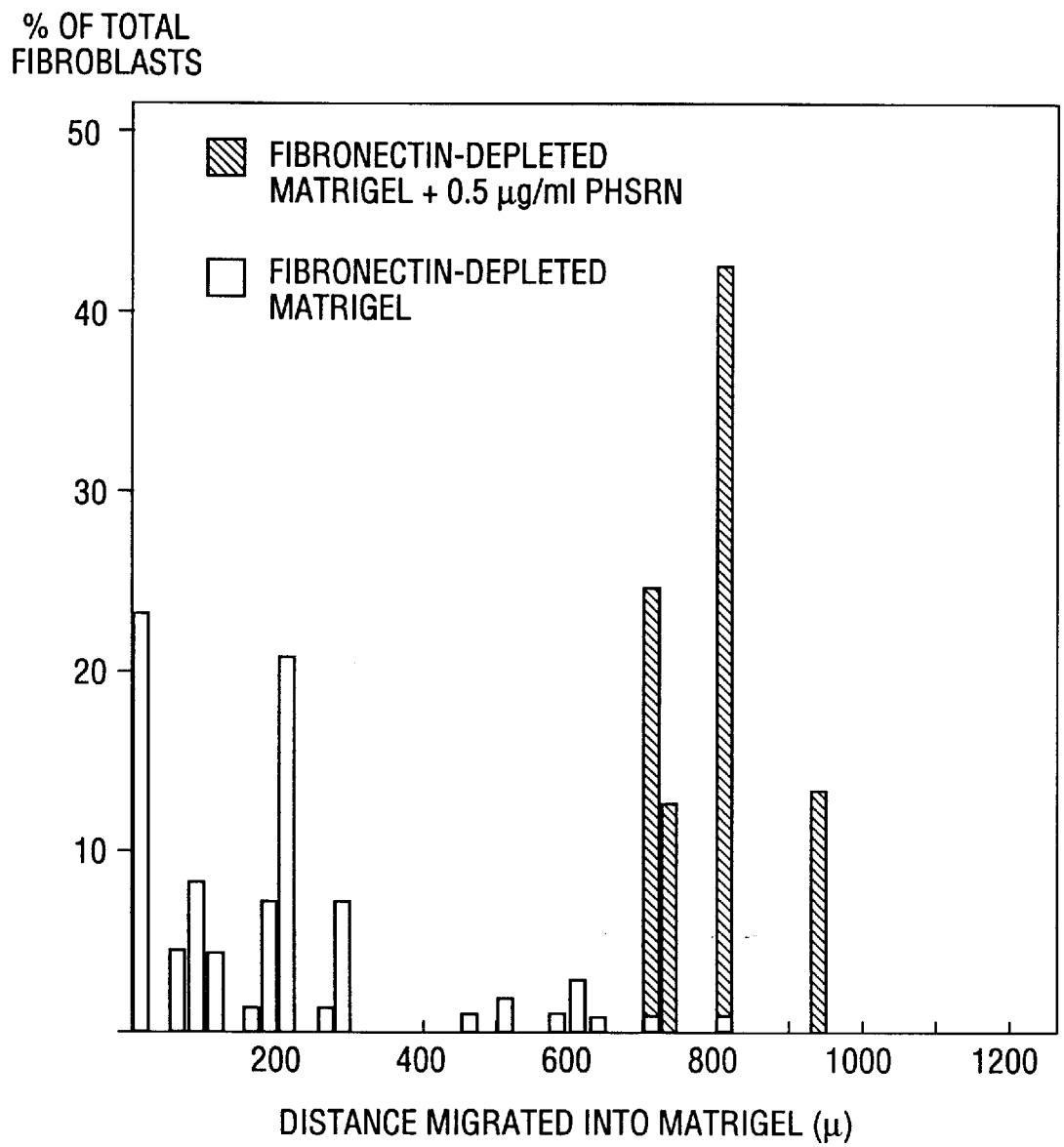
FIG. 4 is a graph showing the results of the testing of normal cells on fibronectin-depleted substrates in vitro with and without invasion-inducing agents according one embodiment of the method of the present invention.

In this example, normal, neonatal fibroblasts were tested on the depleted Matrigel material prepared according to Example 3 above (i.e. antibody depletion). As shown in FIG. 4, panning with an antibody after geletin depletion improved the method for removal, as measured by the reduced invasiveness of fibroblasts. On the other hand, invasiveness of the fibroblasts could be induced by the addition of the PHSRN peptide.

The success of antibody panning suggests the feasibility of removing other components by the antibody panning methods. Other serum components, such as thrombospondin, growth factors and cytokines are contemplated by the present invention for removal by the appropriate (commercially available) antibody.

EXAMPLE 7

Conjugation of PHSRN-containing Peptides

In this example, the preparation of a peptide conjugate is described. The synthetic peptide $NH_2$-PHSRNC can be prepared commercially (e.g. Multiple Peptide Systems, San Diego, Calif.). The cysteine is added to facilitate conjugation to other proteins.

In order to prepare a protein for conjugation (e.g. BSA), it is dissolved in buffer (e.g., 0.01 M $NaPO_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM $NaPO_4$, pH 7.0 buffer. Peak fractions are pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

From the above, it should be clear that the present invention provides a method of testing a wide variety of tumor types, and in particular identifying invasive tumors. With a means of identifying such tumors (now provided by the present invention) and distinguishing such tumors from non-invasive cancer, the physician is able to change and/or optimize therapy. Importantly, the antagonists of the present invention (and other drugs developed by use of the screening assay of the present invention) will provide treatment directed an invasive cells (and therefore associated with minimal host toxicity).

---

I claim:

1. A method of testing human cancer comprising:
   a) providing:
      i) a human cancer patient,
      ii) a fibronectin-depleted substrate, and
      iii) an invasion-inducing agent consisting of a peptide having the sequence PHSRN;
   b) obtaining cancer cells from said patient;
   c) contacting said cells ex vivo with said fibronectin-free substrate and said invasion-inducing agent; and
   d) measuring the extent of cancer cell invasion of said substrate.

2. The method of claim 1, wherein said cancer cells are obtained from a biopsy.

3. The method of claim 1, wherein said cancer cells are selected from the group consisting of breast cancer cells, prostate cancer cells, and colon cancer cells.

4. The method of claim 1, wherein said cancer cells are cultured in serum-free media.

5. The method of claim 1, wherein said fibronectin-depleted substrate is such that cancer cells are not capable of invading said substrate in the absence of said invasion-inducing agent.

6. A method of screening anticancer drugs comprising:
a) providing:
   i) inducible tumor cells,
   ii) a fibronectin-depleted substrate,
   iii) one or more invasion-inducing agents, and
   iv) a candidate drug inhibitor of tumor cell invasiveness;
b) contacting said cells in vitro with said fibronectin-free substrate, said one or more invasion-inducing agents and said candidate drug inhibitor; and
c) measuring the extent of tumor cell invasion of said substrate.

7. The method of claim 6, wherein said cells invade said substrate.

8. The method of claim 6, wherein said inducible cells are selected from the group consisting of breast cancer cells, prostate cancer cells, and colon cancer cells.

9. The method of claim 6, wherein said cancer cells are cultured in serum-free media.

10. The method of claim 6, wherein said invasion-inducing agent comprises a fibronectin-derived peptide.

11. The method of claim 10, wherein said peptide comprises the amino acid sequence PHSRN (SEQ ID No. 1).

* * * * *